(12) United States Patent
Günther et al.

(10) Patent No.: US 6,238,421 B1
(45) Date of Patent: May 29, 2001

(54) INDUCTION HEATING DEVICE AND METHOD FOR METALLIC IMPLANTS IN LIVING BEINGS

(76) Inventors: Rolf. W. Günther, Brüssler 73 c, Aachen (DE), 52074; Thomas Schmitz-Rode, Kupferstrasse 5, Aachen (DE), 52070

( * ) Notice: Subject to any disclaimer, the term of this patent is extended or adjusted under 35 U.S.C. 154(b) by 0 days.

(21) Appl. No.: 08/911,658

(22) Filed: Aug. 15, 1997

(51) Int. Cl.[7] ........................................................ A01N 1/40
(52) U.S. Cl. ............................ 607/13; 607/96; 607/101; 607/102
(58) Field of Search .............................. 607/96, 101, 102, 607/76; 600/13

(56) References Cited

U.S. PATENT DOCUMENTS

| 4,448,198 | * | 5/1984 | Turner | 607/76 |
|---|---|---|---|---|
| 4,633,875 | * | 1/1987 | Turner | 607/76 |
| 5,010,897 | * | 4/1991 | Leveen | 607/101 |
| 5,160,828 | * | 11/1992 | Olsen | 607/101 |
| 5,713,941 | * | 2/1998 | Robins et al. | 607/96 |

FOREIGN PATENT DOCUMENTS

| 2254004 | * | 9/1992 | (GB) | 607/96 |
|---|---|---|---|---|
| 9412101 | * | 6/1994 | (WO) | 607/96 |

* cited by examiner

Primary Examiner—Robert L. Nasser, Jr.
(74) Attorney, Agent, or Firm—Merchant & Gould P.C.

(57) ABSTRACT

A system and method for heating cells surrounding metallic implants in living beings. The system includes a metallic implant within the living being, surrounded by the cells to be heated, an induction coil having an aperture sufficiently large to accommodate a portion of the living being containing the metallic implant, and an RF generator coupled to the coil to apply an electric RF signal thereto, the RF signal ranging in frequency from 10 kilohertz to 10 megahertz. The metallic implant is inductively heatable by the application of the RF signal to the induction coil.

33 Claims, 1 Drawing Sheet

INDUCTION HEATING DEVICE AND METHOD FOR METALLIC IMPLANTS IN LIVING BEINGS

FIELD OF THE INVENTION

The present invention is directed to a device and method for use with metal implants in living beings to heat cells immediately surrounding a metallic implant. The device and method can be used, for example, for treatment of hyperplastic cell growth conditions.

BACKGROUND OF THE INVENTION

Metallic implants are successfully used inside living beings for many purposes. For example, stents, or tubular endoprosthesises, are used in the human vascular system to widen or prevent further narrowing, or stenosis, caused by arteriosclerosis. A stent is often placed in a vessel after an angioplasty. Angioplasty is a known procedure for widening a vessel, but may cause trauma resulting in longitudinal ruptures in the intima. Application of a stent to the region of the angioplasty provides a continuous widening force on the vessel wall. However, the damaged blood vessel can react by generating cells to repair itself. In some cases, excessive cell generation, termed "intimal hyperplasia," occurs at the intima surrounding the stent. Intimal hyperplasia is the abnormal multiplication of normal cells in an abnormal cell arrangement in the tissue. Hyperplasia may result in a re-narrowing of the blood vessel, or restenosis.

Metallic implants can also be used to palliatively treat the narrowing of hollow organs caused by tumors. For example, tumors near the trachea, esophagus, biliary ducts, or urinary tract can press upon and narrow these organs. A stent can be placed in the organ to preserve its shape and function. A stent is typically constructed of frame of material, called a stent matrix, which includes a pattern of interstices. The tumor may eventually grow into the stent, through these interstices, thus causing narrowing of the stented hollow organ. As a result, continued growth of the tumor may overcome the palliative effect of the stent.

Aneurysms, internal bleeding of vessels, leakages of vessels, and tumorous vessels can be occluded by metallic implants, such as metallic spirals or stents, put in over catheters to seal the vessel leak. However, complete occlusion is not always achieved because blood leakage may continue through spaces in the spiral or stent matrix following the placement of the stent in the vessel. Therefore, the aneurysm, for example, may continue to grow despite the presence of the implant, and the bleeding may not be completely stopped. Currently, stents covered with DACRON® material are often used to seal an aneurysm. However, the stents covered with DACRON® material are thick and therefore require a large introduction site and may stretch the vessel wall considerably.

Therefore, a device and treatment method are needed which reduce the excessive tissue reaction, for example, in restenosis following angioplasty. There is also a need for a device and treatment method for reducing the excrescence of tumor cells surrounding metallic implants. Further, a device and treatment method are needed to complete a vascular occlusion by metallic implants without invasive procedures.

SUMMARY OF THE INVENTION

The invention provides a system for heating cells surrounding a metallic implant implanted in a living being, comprising an RF generator to generate an RF signal. The system also includes an induction coil coupled to the RF generator to receive the RF signal therefore, the coil having an aperture therethrough sufficiently wide to receive a portion of the living being so that the metallic implant is locatable within the coil, and a controller coupled to the generator to control the RF signal applied to the coil. According to the invention an RF induction signal at a location within the coil is operative to inductively heat a metallic implant placed within the coil.

The invention also describes a method for heating cells surrounding a metallic implant in a living being, the method comprising inductively heating the metallic implant to a temperature sufficient to heat the cells.

The above summary of the present invention is not intended to describe each illustrated embodiment or every implementation of the present invention. The figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
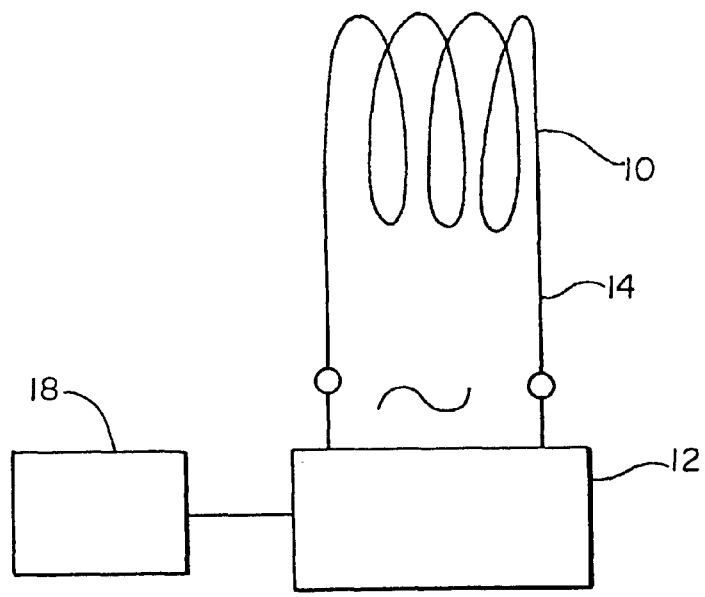
FIG. 1 is an electrical schematic diagram of the system of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE VARIOUS EMBODIMENTS

The present invention claims priority to DE 295 19 982.2, the disclosure of which is incorporated herein.

The present invention is applicable to prolonging and improving the medical use of metallic implants in living beings. Metallic implants are pieces of metal that are placed within a living being. A metal is defined as a material that is inductively heatable according to the present invention. A metal is an electrically conductive material. The invention is advantageous where excessive tissue reaction occurs surrounding metallic implants or where there is an excrescence of tumor cells surrounding metallic implants. The invention is also useful where there is an uncompleted vascular occlusion by metallic implants. While the present invention is not so limited, an appreciation of the various aspects of the invention will be provided through a discussion of various application examples operating in such an environment. The device and method disclosed are suitable for human or animal use.

By heating cells at the site of intimal hyperplasia, excessive cell generation in a vessel wall following angioplasty can be reduced so that the narrowing effects associated with vascular restenosis post angioplasty are reduced.

Further, heating cells that grow into a stent at a stented hollow organ can reduce the expansion of the tumor into that area, thereby maintaining the integrity of the passage for a longer time period.

Heating a metallic implant inside a living being raises the temperature of the living cells that immediately surround the implant. If the rise in temperature is sufficiently large, the cells will shrink and cell generation will slow or stop. By heating the implant inductively, this localized thermal cell damage of the cells in the immediate neighborhood of the implant can be achieved without requiring an invasive procedure. Thus, the advantages discussed above can be realized using a noninvasive technique. A conducting coil and an RF generator are used in the present invention to heat a metallic implant inductively from outside the body. The metallic implant then heats the surrounding cells by conduction. Raising the cell temperature to above 45° C., or more particularly to a range of approximately 50° C. to 65° C., achieves the desired localized cell damage according to the present invention.

Figure 2:
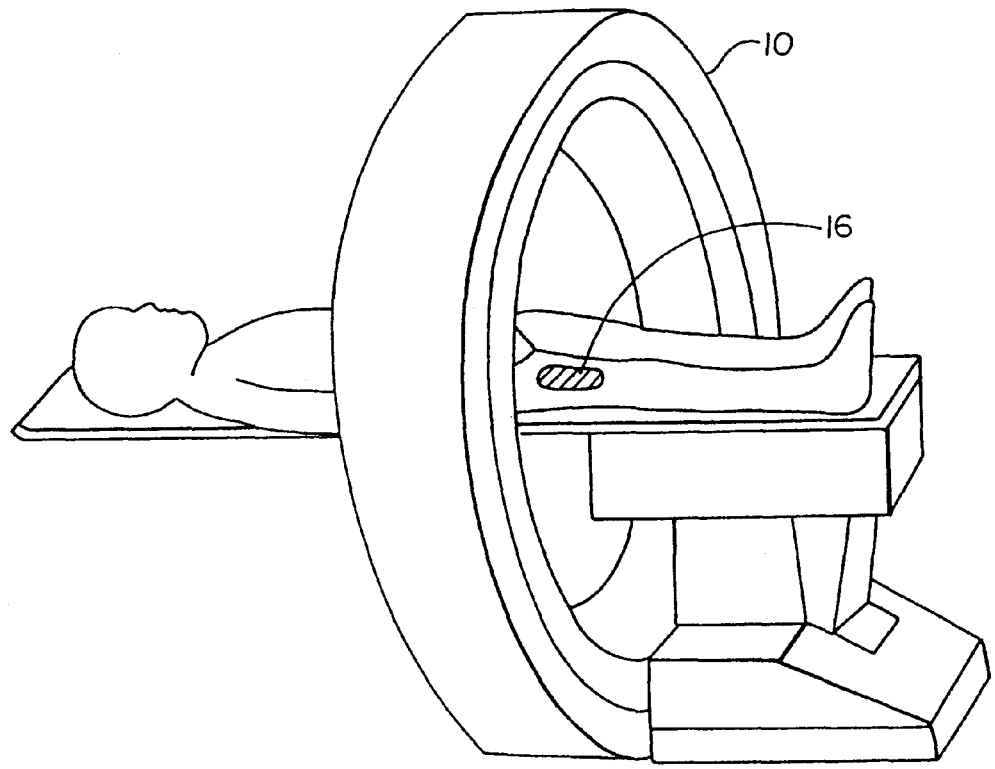
FIG. 2 is a view of the system of the present invention.

FIG. 1 illustrates one embodiment of the disclosure in which an inductive coil 10 and a generator 12 are shown. The coil includes several windings with an electrical conductor 14, for example, copper wire or copper tubing. The coil 10 has an inner opening or aperture sufficiently large to permit a portion of the body with a metallic implant 16, or metallic endoprosthesis, to be placed within the coil, as shown in FIG. 2. The body part having the metallic implant 16 may be positioned approximately near the center axis of the coil 10.

An RF electric signal is applied to the coil 10, creating an alternating magnetic field in the space inside the coil 10. The alternating magnetic field creates changing electric fields in the implant 16. As electrons flow across regions of the metal to equalize the electric charge across different regions, eddy currents are excited in the metal and flow within the metallic implant 16. The eddy currents heat the metallic implant 16 due to resistive heating.

The amount of heat produced by the eddy currents depends on the frequency and power of the electric signal applied to the coil and duration of exposure to the magnetic fields. Suitable materials for a metallic implant, such as a stent, include stainless steel, nickel titanium, alloys including nickel, titanium, vanadium, and/or chromium, and other biocompatible metals. The goal of the inductive heating is to raise the temperature of the cells surrounding a stent matrix so that the cells will shrink and cell generation will slow. The temperature may be raised to above 45° C. or, more particularly, to 50° C. to 65° C., where heat damage and cell death may be induced.

A pulsed RF signal may be applied to the coil 10 at repetitive intervals. A controller may be coupled to the generator to control the application of the RF signal to the coil in the desired manner. The duration of each pulse may range from 1 millisecond to 100 seconds, more particularly from 10 milliseconds to 1 second. The pulse rate of the RF signal may range from approximately 100 Hz to 0.1 Hz, more particularly from 10 Hz to 0.1 Hz. In one particular example, an RF pulse lasting for 100 milliseconds, may be applied five times per second. It will be appreciated that other pulse lengths and repetition rates may be employed to achieve the desired heating. Also, the RF signal may be continuously applied.

The RF signal, pulsed or continuous, may be applied for a duration of approximately 0.1 to 30 seconds or, in other embodiments, approximately 5 to 20 seconds, or approximately 3 to 15 seconds. It will be appreciated that the time of application, duration of pulse, frequency of the signal, power of the signal, and other variables may be adjusted in various combinations to achieve the desired heating of the metallic implant.

The generator preferably produces a radio frequency signal of 10 kilohertz to 10 megahertz. In one particular embodiment, the generator applies a signal having a frequency in the range of 30 kHz to 1 MHz. When the frequency of the RF signal is outside the range 30 kHz to 1 MHz, the inductive heating effect decreases. It has been found that the temperature of a stent does not significantly increase when subjected to the RF field of a magnetic resonance imaging system, typically having a frequency in the range of 20 MHz to 70 MHz, varying with the magnetic field strength employed.

The peak power of the RF signal applied to the coil may range from 1 kW to 1 MW, while in one particular embodiment, the peak power ranges from 5 kW to 20 kW. In another embodiment, the peak power is approximately 15 kW.

The inner aperture of the coil used may range in size from 3 cm to 1 m across, more particularly from 4 cm to 60 cm. When a coil having a smaller aperture is used,. for example, of 4 cm, it is important that the implant to be inductively heated is positioned centrally within the coil. In a coil with an average diameter of 4 cm, the inductive heating effect decreasees substantially as the metallic implant is moved away from the center of the aperture. The coil will consist of a conductive material, and could be wire or tubing, for example. If tubing is used, water may flow through the tubing for cooling, if necessary.

Experiments have been conducted to test the efficacy of the induction coil in heating a metal implant. In these experiments, stents surrounded by biological tissue were used as the implants. In some cases, the tissue comprised cells cultivated on the stent matrix itself, for example, tumor cells. In other experiments, the stent was first implanted in a blood vessel of an animal, and the portion of the vessel containing the stent was then harvested from the animal. Typically, the mass of vessel tissue was approximately 20 grams.

The diameter of the stents used in these experiments typically ranged from about 8 to 12 mm, and from about 1 to 3 cm in length. Prior to exposure to the inductive RF field, the stent and tissue were placed in about 10 ml of saline solution to approximate the thermally conductive environment of the body.

The RF generator used in these experiments produced an RF signal having a frequency of about 300 kHz, and at a peak power of 15 kW. The generator was typically operated in a pulsed mode, producing a 100 ms pulse at a repetition rate of 5 pulses per second. Thus the average power applied to the coil was 7.5 kW. The samples were exposed to the pulsed RF signal for a duration of between 3 and 15 seconds.

The coil used in the experiments was formed from copper tubing having a diameter of approximately 10 mm, with a wall thickness of 2 mm. The coil had five turns of wire and had an average diameter of 4 cm. The length of the coil along its longitudinal axis was 7 cm. Cooling the tubing by water was not necessary in this device.

It was found that, under the conditions described above, the temperature of the tissue samples surrounding the stents increased to a temperature ranging from 50° C. to 65° C. Necrosis of the cells was observed after the temperature was raised to this range.

When the implant is heated, living cells surrounding the implant, or metallic stent matrix, are heated, and may be thermally damaged. The extent of the area of cells heated is at least partially regulated by the duration of the exposure to the RF field. The temperature of these cells is raised because heat from the selectively heated implant is conducted into the surrounding tissue. The nuclei and cytoplasm of the neighboring cells shrink as a result of the conducted heat. It will be appreciated that a variation in the temperature of the heated implant results in a variation in the range of damage surrounding the implant. If the body of a living being is exposed in an induction heating device at frequency ranging from 30 kHz–1 MHz, a metallic implant is heated selectively and there is no measurable increase in the temperature of normal body tissue.

The method of the present invention may be used repeatedly during a course of fractionated therapy. The metallic implant may be inductively heated periodically to prevent the occurrence of restenosis, for example, over periods of weeks or months.

The method of the invention can be used to heat cells immediately surrounding metallic implants for the purposes of, for example, reducing excessive tissue reaction in the vascular system following stent implantation.

The method may also be used for preventing the excrescence of tumor cells surrounding metallic implants.

Another application of the present invention is to complete occlusion of a stented aneurysm when, for example, a stent is used at an aneurysm site. Typically, a stent has a matrix of interstitial spaces in the stent wall. Blood leakage may continue through these spaces following the placement of the stent in the vessel. By a controlled warming process of the stent according to the present invention, the formation of thrombi can be encouraged in the holes of the stent. An accumulation of thrombi and fibers over the stent blocks further leakage through the aneurysm. Therefore, where an implant is used to occlude an aneurysm and the implant is heated, a clot may be encouraged to form at the aneurysm site, thereby preventing further bleeding through the vessel wall. One concern with this application is that small thrombi might form at the edges of the stent matrix and break free from the stent.

While the invention is amenable to various modifications and alternative forms, specifics thereof have been shown by way of example in the drawings and will be described in detail. It should be understood, however, that the intention is not to limit the invention to the particular embodiments described. On the contrary, the invention is to cover all modifications, equivalents, and alternatives falling within the spirit and scope of the invention as defined by the appended claims. For example, the term metallic implant that is used in connection with this invention includes devices other than stents, such as embolization coils, metallic particles used for embolization purposes, and other metallic devices, implants, and endoprotheses.

What is claimed is:

1. A system for heating cells in a living being, the system comprising:
    a metallic stent for implanting within the living being, the metallic stent surrounded by the cells to be heated;
    an induction coil having an aperture of a size sufficiently large to accommodate a portion of the living being containing the metallic implant; and
    an RF generator coupled to the coil to apply an electric RF signal thereto, the RF signal ranging in frequency from 10 kilohertz to 10 megahertz;
    wherein the metallic implant is inductively heatable by the application of the RF signal to the induction coil.

2. The system of claim 1, wherein the signal has a frequency ranging from 30 kilohertz to 1 megahertz.

3. The system of claim 1, wherein the coil has an average diameter ranging from 3 to 100 centimeters.

4. The system of claim 1, further comprising a controller coupled to the generator to pulse the RF signal applied to the coil.

5. The system of claim 4, wherein a pulse rate ranges from 100 Hertz to 0.1 Hertz.

6. The system of claim 4, wherein a pulse of RF signal has a duration ranging from 1 millisecond to 100 seconds.

7. The system of claim 1, wherein the RF signal has a peak power ranging from 1 kW to 1 MW.

8. The system of claim 1, wherein the RF signal has a peak power of 15 kW.

9. The system of claim 1, further comprising a platform to support the portion of the living being within the induction coil.

10. A system for heating cells surrounding a stent implanted in a living being, the system comprising:
    a metallic stent, the metallic stent implanted in the living being;
    an RF generator to generate an RF signal having a frequency in the range of approximately 10 kilohertz to 10 megahertz and a peak power in the range of approximately 1 kW to 1 MW;
    an induction coil coupled to the RF generator to receive the RF signal therefore, the coil having an aperture therethrough having a size sufficient to receive a portion of the living being so that the stent is locatable within the coil; and
    a controller coupled to the generator to control the RF signal applied to the coil;
    wherein an RF induction signal at a location within the coil is operative to inductively heat a stent placed within the coil.

11. The system of claim 10, wherein the controller applies the RF signal to the coil at a pulsed rate ranging from 100 Hertz to 0.1 Hertz.

12. The system of claim 10, wherein the controller applies the RF signal to the coil at a pulsed rate, each pulse having a duration ranging from 1 millisecond to 100 seconds.

13. The system of claim 10, wherein the RF signal has a peak power of 15 kW.

14. The system of claim 10, further comprising a platform to support the portion of the living being within the induction coil.

15. A system for treating intimal hyperplasia by heating cells surrounding a stent implanted in a living being, the system comprising:
    a metallic stent, the metallic stent implanted in the living being;
    an RF generator to generate an RF signal having a frequency in the range of approximately 10 kilohertz to 10 megahertz and a peak power in the range of approximately 1 kW to 1 MW;
    an induction coil coupled to the RF generator to receive the RF signal therefore, the coil having an aperture therethrough having a diameter sufficient to receive a portion of the living being so that the stent is locatable within the coil; and
    a controller coupled to the generator to control the RF signal applied to the coil;
    wherein an RF induction signal at a location within the coil is operative to inductively heat a stent placed within the coil.

16. A method for heating cells surrounding a metallic stent implanted in a living being, the method comprising inductively heating the metallic stent to a temperature sufficient to heat the cells.

17. The method of claim 16, wherein the step of inductively heating further comprises applying an RF signal to an inductive coil having an aperture therethrough, where a portion of the living being containing the metallic implant is located in the aperture.

18. The method of claim 17, wherein the RF signal has a frequency ranging from approximately 1 kilohertz to 10 megahertz.

19. The method of claim 17, wherein the RF signal has a frequency ranging from approximately 30 kilohertz to 1 megahertz.

20. The method of claim 17, wherein the application of the RF signal to the coil is pulsed.

21. The method of claim 20, wherein the application of the RF signal to the coil has a pulse rate ranging from approximately 100 Hertz to 0.1 Hertz.

22. The method of claim 20, wherein the application of the RF signal to the coil has a pulse duration ranging from approximately 1 millisecond to 100 seconds.

23. The method of claim 17, wherein the RF signal applied to the coil has a peak power ranging from approximately 1 kW to 1 MW.

24. A method for heating cells surrounding a metallic stent in a living being, the method comprising:
   positioning the living being so that the metallic stent is located substantially within an aperture of an inductive coil; and
   applying an RF signal to the coil, so that the metallic stent is inductively heated with the living being;
   wherein the RF signal applied to the coil is pulsed.

25. The method of claim 24, wherein the RF signal applied to the coil has a frequency ranging from approximately 1 kilohertz to 10 megahertz.

26. The method of claim 24, wherein the RF signal applied to the coil has a frequency ranging from approximately 30 kilohertz to 1 megahertz.

27. The method of claim 24, wherein the RF signal is applied to the coil for at least 5 seconds and not more than 20 seconds.

28. The method of claim 24, wherein the application of the RF signal to the coil has a pulse rate ranging from approximately 100 Hertz to 0.1 Hertz.

29. The method of claim 24, wherein the application of the RF signal to the coil has a pulse duration ranging from approximately 1 millisecond to 100 seconds.

30. The method of claim 24, wherein the RF signal applied to the coil has a peak power ranging from approximately 1 kW to 1 MW.

31. A method for preventing intimal hyperplasia at a site of an angioplasty, comprising:
   implanting a metallic implant at the site of the angioplasty; and
   inductively heating the implant to a temperature sufficient to heat the cells surrounding the implant.

32. The method of claim 31, further comprising repeating the inductive heating step at regular intervals.

33. A method for complete exclusion of an aneurysm, comprising:
   positioning a metallic implant defining interstitial spaces at a site of the aneurysm;
   inductively heating the metallic implant to a temperature sufficient to induce formation of thrombi in the interstitial spaces of the metallic implant.

* * * * *